United States Patent
Lehmann et al.

(10) Patent No.: US 11,241,265 B2
(45) Date of Patent: Feb. 8, 2022

(54) DEVICE AND METHOD FOR ESTABLISHING AN ANCHORAGE IN TISSUE

(71) Applicant: Woodwelding AG, Stansstad (CH)

(72) Inventors: Mario Lehmann, Les Pommerats (CH); Andrea Muller, Winterthur (CH); Urs Weber, Evilard (CH); Philipp Seiler, Niederdorf (CH)

(73) Assignee: WOODWELDING AG, Stansstad (CH)

(*) Notice: Subject to any disclaimer, the term of this patent is extended or adjusted under 35 U.S.C. 154(b) by 248 days.

(21) Appl. No.: 16/454,480

(22) Filed: Jun. 27, 2019

(65) Prior Publication Data

US 2019/0314074 A1 Oct. 17, 2019

Related U.S. Application Data

(62) Division of application No. 14/953,951, filed on Nov. 30, 2015, now Pat. No. 10,363,077, which is a (Continued)

(51) Int. Cl.
*A61B 17/88* (2006.01)
*A61B 17/04* (2006.01)
(Continued)

(52) U.S. Cl.
CPC .... *A61B 17/8811* (2013.01); *A61B 17/00491* (2013.01); *A61B 17/0401* (2013.01);
(Continued)

(58) Field of Classification Search
None
See application file for complete search history.

(56) References Cited

U.S. PATENT DOCUMENTS 3,284,257 A * 11/1966 Roberts ............... D06H 5/00
156/73.1
5,372,665 A * 12/1994 Chafin ............... B29C 35/0261
156/155

(Continued)

FOREIGN PATENT DOCUMENTS

WO 2005/079696 9/2005
WO 2007/092869 8/2007
(Continued)

*Primary Examiner* — Zade Coley
(74) *Attorney, Agent, or Firm* — Rankin, Hill & Clark LLP

(57) ABSTRACT

A perforated sheath is anchored in a tissue opening with the aid of a tool, wherein the anchorage is achieved with the aid of mechanical vibration and a material which is liquefiable by the vibration. The tool includes a vibrating element and a counter element. Distal portions of both elements are introduced into the sheath to be in contact with each other at an interface. The vibrating element is connected to a vibration source and the vibrating element and the counter element are held against each other for effecting liquefaction of the liquefiable material at the interface. Under the effect of the force applied to the vibrating and counter element for holding them against each other, the liquefied material flows from the interface through the sheath perforation and penetrates the tissue.

6 Claims, 8 Drawing Sheets

Related U.S. Application Data division of application No. 12/990,036, filed as application No. PCT/CH2009/000138 on Apr. 30, 2008, now Pat. No. 9,226,784.

(60) Provisional application No. 61/049,587, filed on May 1, 2008.

(51) Int. Cl.
    *A61B 17/68*     (2006.01)
    *A61B 17/86*     (2006.01)
    *A61B 17/80*     (2006.01)
    *A61B 17/00*     (2006.01)
    *A61F 2/30*     (2006.01)
    *A61B 17/90*     (2006.01)

(52) U.S. Cl.
CPC .......... *A61B 17/686* (2013.01); *A61B 17/809* (2013.01); *A61B 17/864* (2013.01); *A61B 17/8819* (2013.01); *A61B 17/8836* (2013.01); *A61B 17/90* (2021.08); *A61B 2017/005* (2013.01); *A61B 2017/00411* (2013.01); *A61B 2017/00955* (2013.01); *A61B 2017/042* (2013.01); *A61B 2017/044* (2013.01); *A61B 2017/0409* (2013.01); *A61B 2017/0422* (2013.01); *A61B 2017/0424* (2013.01); *A61B 2017/883* (2013.01); *A61B 2017/8813* (2013.01); *A61F 2002/30065* (2013.01); *A61F 2210/0071* (2013.01)

(56) References Cited

U.S. PATENT DOCUMENTS

| | | | | |
|---|---|---|---|---|
| 5,666,779 A * | 9/1997 | Fuchs | ................ | F16B 13/0833 52/705 |
| 5,993,458 A * | 11/1999 | Vaitekunas | ........ | A61B 17/0401 606/104 |
| 6,080,161 A * | 6/2000 | Eaves, III | .............. | A61B 17/68 606/329 |
| 7,008,226 B2 * | 3/2006 | Mayer | ..................... | A61F 2/447 433/173 |
| 7,329,263 B2 * | 2/2008 | Bonutti | .............. | A61B 17/0487 606/139 |
| 7,335,205 B2 * | 2/2008 | Aeschlimann | ........ | B29C 65/601 606/232 |
| 8,225,479 B2 * | 7/2012 | Clinch | .................. | B29C 66/636 29/525.05 |
| 2004/0030341 A1 * | 2/2004 | Aeschlimann | ........ | B29C 66/727 606/232 |
| 2004/0038180 A1 * | 2/2004 | Mayer | ..................... | A61B 17/70 433/173 |
| 2004/0206443 A1 * | 10/2004 | Monsheimer | ....... | B29C 66/7234 156/73.1 |
| 2006/0105295 A1 * | 5/2006 | Mayer | .................. | A61C 8/0012 433/173 |
| 2008/0021474 A1 * | 1/2008 | Bonutti | .............. | A61B 17/7062 606/64 |
| 2008/0109080 A1 * | 5/2008 | Aeschlimann | ..... | A61B 17/8872 623/16.11 |
| 2008/0262517 A1 * | 10/2008 | Wieland | ............... | A61B 17/846 606/151 |
| 2009/0018590 A1 * | 1/2009 | Dorawa | ............... | A61B 17/864 606/301 |
| 2009/0131947 A1 | 5/2009 | Aeschlimann et al. | | |
| 2011/0046670 A1 * | 2/2011 | Lehmann | ........... | A61B 17/0401 606/232 |

FOREIGN PATENT DOCUMENTS

| | | | | |
|---|---|---|---|---|
| WO | 2008/034276 | 3/2008 | | |
| WO | 2008/034277 | 3/2008 | | |
| WO | WO-2008034277 A2 * | 3/2008 | .......... | A61B 17/686 |
| WO | 2009/117837 | 10/2009 | | |
| WO | WO-2009117837 A1 * | 10/2009 | .......... | A61B 17/866 |

\* cited by examiner

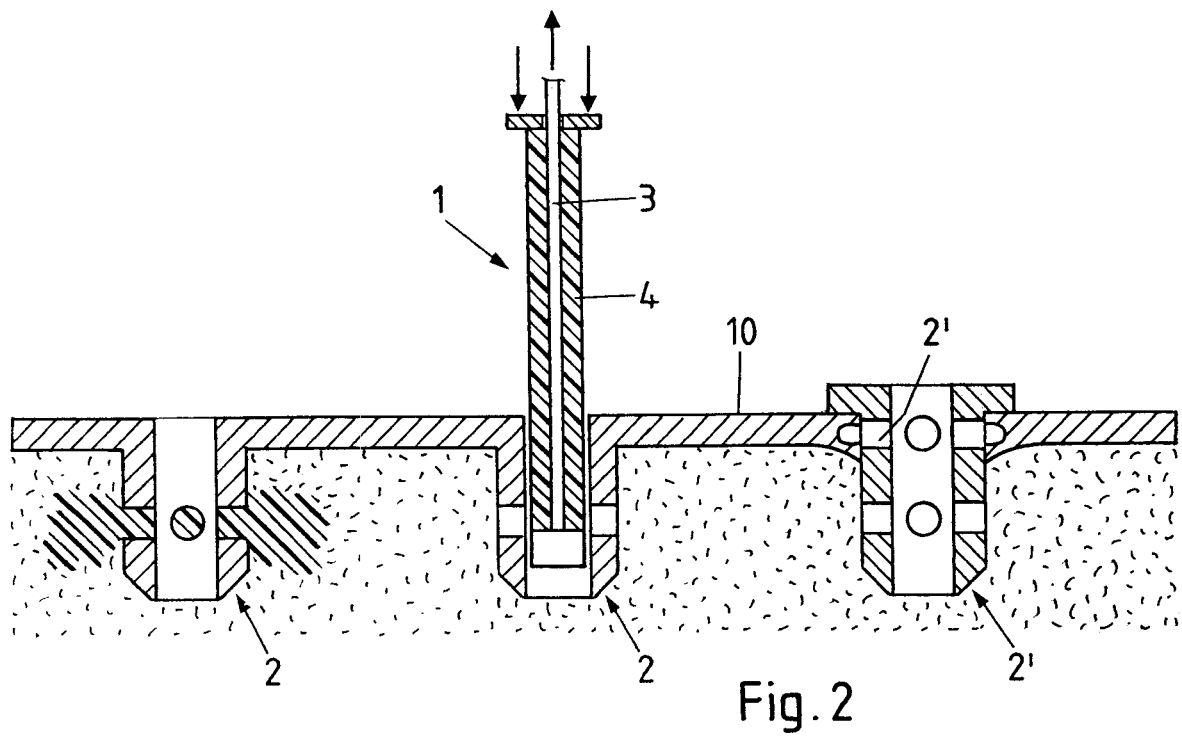
Fig. 2
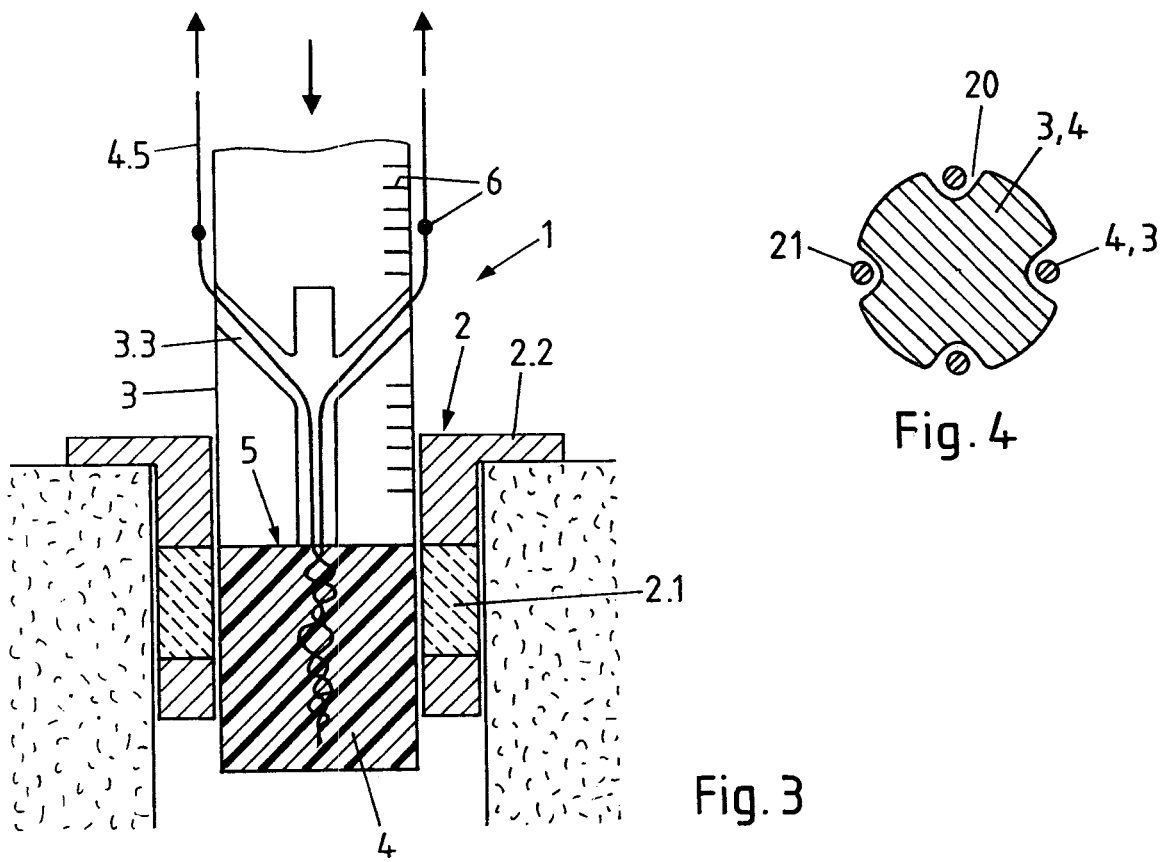
Fig. 3
Fig. 4

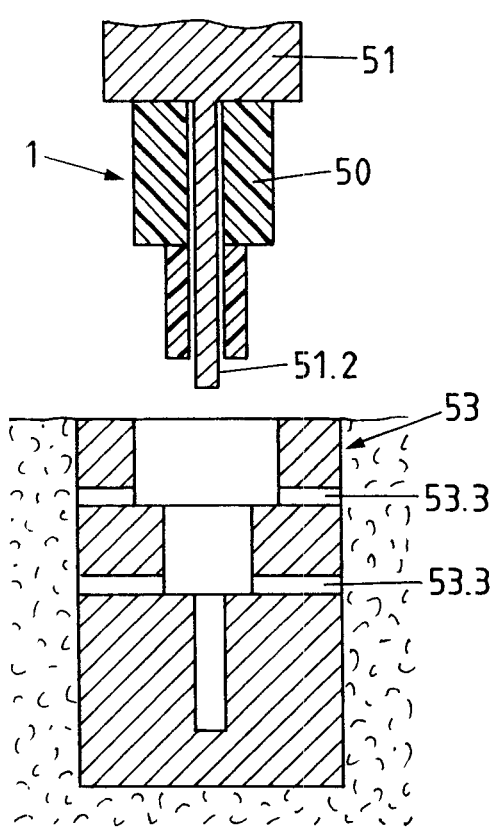
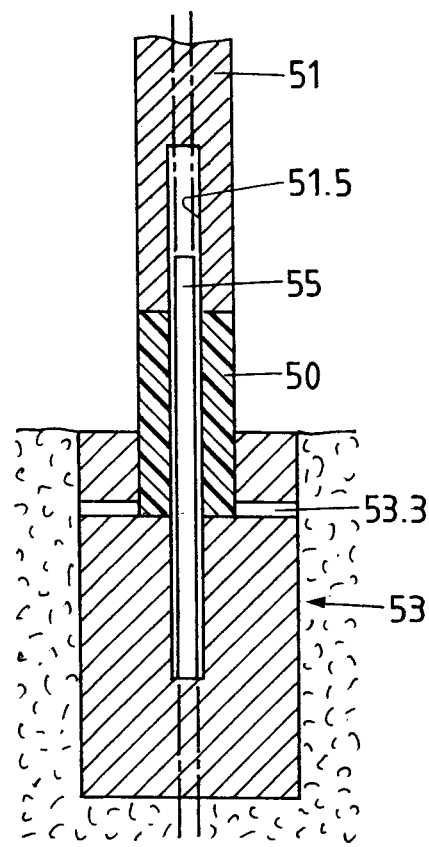
Fig. 16            Fig. 17
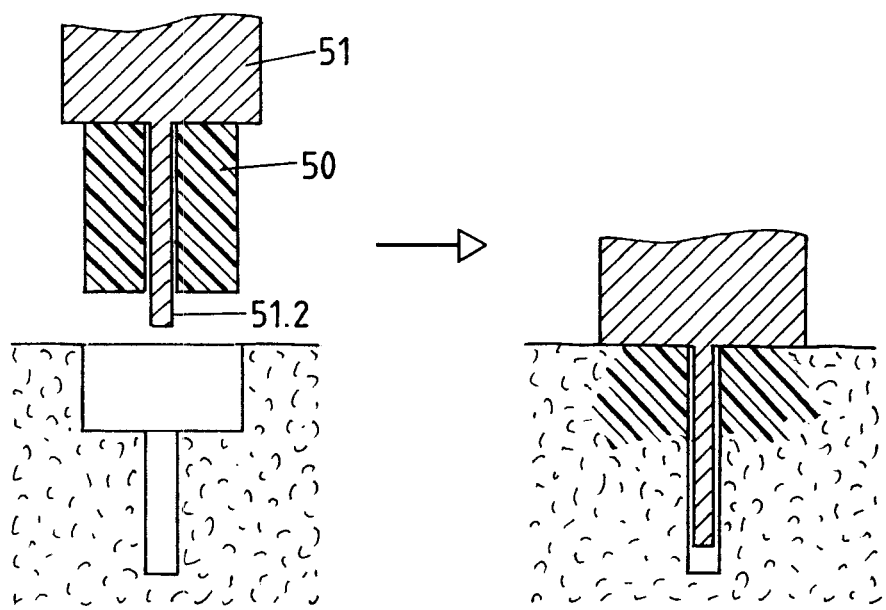
Fig. 18

DEVICE AND METHOD FOR ESTABLISHING AN ANCHORAGE IN TISSUE

The invention is in the field of medical technology and concerns a device and a method for establishing an anchorage in tissue, in particular in hard tissue such as e.g. bone tissue.

Devices to be anchored in bone tissue range from fasteners to endoprostheses. The fasteners may serve e.g. for fastening a suture or wire in a bone, for reattaching a tendon, ligament or bone fragment to a bone from which it has been torn or broken off, for fixing plates and rods relative to a bone which may be fractured, dislocated or dissected, or relative to bones which need stabilization relative to each other, or for attaching drug delivery elements on a bone. Endoprostheses replace tissue parts, they are e.g. joint prostheses, resurfacing implants or dental implants.

There are many known methods for anchoring the named devices in the bone tissue, the most common ones consisting in equipping the device with a thread and anchoring it in the bone by screwing it into the bone tissue, in using a curable cement, in pressing the device into a tissue opening which is smaller than the device (press fit), or in using mechanical vibration, preferably ultrasonic vibration, and a material having thermoplastic properties and being liquefiable by the mechanical vibration. The last mentioned method and corresponding devices are disclosed e.g. in the publications U.S. Pat. Nos. 7,335,205, 7,008,226, WO-2005/079696, or WO-2008/034277 which are enclosed herein by reference.

The basis of all anchoring methods using mechanical vibration and a thermoplastic material, which is able to be liquefied by the mechanical vibration, is the in situ liquefaction of a thermoplastic material having, in its solid state, mechanical properties sufficient for producing a mechanically satisfactory anchorage, wherein the liquefied material has a viscosity which allows the material to penetrate natural or beforehand provided pores, cavities or other structures of the tissue and wherein an only relatively small amount of the material needs to be liquefied such that no unacceptable thermal load is put on the tissue. When re-solidified, the thermoplastic material which has penetrated the pores, cavities or other structures constitutes a positive fit connection with the tissue.

Suitable liquefaction is achieved by using materials with thermoplastic properties having a modulus of elasticity of at least 0.5 GPa and a melting temperature of up to about 350° C. and by providing such material at an interface between a vibrating element and a counter element being held against each other, wherein the vibration preferably has a principal direction perpendicular to the orientation of the interface but may also be directed substantially parallel thereto and wherein the vibration preferably has a frequency of between 2 and 200 kHz (ultrasonic vibration). Due to the relatively high modulus of elasticity the thermoplastic material transmits ultrasonic vibration with such little damping that inner liquefaction and thus destabilization of the device does not occur, i.e. liquefaction occurs only at the named interface and is therewith easily controllable and can be kept to a minimum.

The named interface is either a contact location between the device to be anchored and a surface of the tissue in which the device is to be anchored, or it is an interface between two device parts. For the first case (interface between device and tissue), this means that the device carries the liquefiable material at a surface which is in contact with the tissue and constitutes the vibrating element, and it further means that the tissue acts as counter element, i.e. needs to be able to withstand the mechanical load being put on such counter element and therefore needs a certain mechanical stability (preferably hard tissue such as bone or dentine) such that it does not yield before liquefaction of the thermoplastic material has at least started. On the other hand, liquefaction takes place exactly where anchorage is to be achieved and can therewith be limited to a minimum amount of the thermoplastic material. In the second case (interface between two device parts) there may not be any necessity for the tissue to bear a mechanical load such that anchorage in nearly any tissue becomes possible, but the liquefied material needs to flow from the named interface to the tissue surface and it is therefore important that the interface is exactly defined and exactly positioned or positionable as close as possible to the tissue in which anchorage is to be achieved. Furthermore it is not necessary that the vibration is transmitted through the liquefiable material to the interface.

The principle of anchorage in tissue with the aid of mechanical vibration and a material which is liquefiable by mechanical vibration is realized up to now in three general ways. The first and simplest way consists in pressing the liquefiable material against the tissue and transmitting the vibration through the liquefiable material to the interface between the tissue and the liquefiable material where liquefaction will occur. The second way consists in pressing the liquefiable material into a perforated sheath, the sheath being supported by the tissue and the vibration being transmitted to the liquefiable material, wherein liquefaction occurs between the inside surface of the sheath and the liquefiable material and wherein the liquefied material will exit from the sheath perforation into the tissue surrounding the sheath. The third way consists in providing the liquefiable material at the interface between a vibrating element and a counter element and arranging this interface close to the tissue such that material which is liquefied at the interface flows from the interface to penetrate the tissue, wherein the small hydrostatic force of the flowing material is the only mechanical load on the tissue.

The above shortly described first and second way are disclosed in the publications U.S. Pat. Nos. 7,335,205, 7,008,226 and WO 2005/079696, the third way in the U.S. application No. 60/983,791, which are all enclosed herein by reference.

It is the object of the invention to provide a further device and method for establishing an anchorage in tissue with the aid of mechanical vibration and a material with thermoplastic properties being liquefiable by the mechanical vibrations.

With a first aspect of the invention, the anchoring process is to be made possible with a minimum of mechanical loading of the tissue such that anchorage can be achieved without problems not only in cancellous and osteoporotic bone tissue but also e.g. in particulate bone replacement or bone graft material, in soft tissue or in larger tissue cavities, which are filled with the material. Furthermore, device and method according to this first aspect of the invention are to render the final position of the anchored device fully independent of the anchoring process such that accurate control of the liquefaction can be easily adapted to local tissue characteristics which may become apparent only during the anchoring process.

The second aspect of the invention regards an improvement of the anchoring process.

These objects are achieved by the devices and the methods as defined in the appended claims.

The basis of the first aspect of the invention is a combination of the second and third of the above briefly discussed three ways to achieve anchorage in tissue with the aid of mechanical vibration and a thermoplastic material which is liquefiable by the mechanical vibration. In other words: liquefaction within a perforated sheath is achieved without the sheath acting as counter element but at an interface between a vibrating element and a counter element being positioned within the sheath, wherein the liquefiable material is preferably comprised by the counter element but may also be comprised by the vibrating element and wherein the force and counterforce for holding the vibrating element and the counter element against each other act from the outside of sheath and tissue and without support from sheath or tissue.

In the following the term "perforated sheath" is to be understood as an item with an inner, e.g. cylindrical, space and with openings connecting this inner space with an outer surface of the sheath, wherein the openings or perforations of the sheath may be constituted by regions made of a material having an open porosity, by a plurality of smallish openings (e.g. bores) or by only one or a very few larger openings (fenestration). Sheaths with more than one inner space are possible also. As mentioned above, the anchoring process puts hardly any mechanical demands on the sheath, which means that the sheath can be rigid or flexible (e.g. made of a textile of sheet material).

For the anchoring process, the perforated sheath is positioned in a tissue opening preferably such that the tissue walls of the opening surround the sheath closely at least in areas in which the sheath is perforated (anchoring locations) and, for the anchoring process, distal portions of the vibrating element and the counter element are positioned in the sheath. During the anchoring process the vibrating element and the counter element are moved against each other for compensating for the liquefied material flowing from the interface through the sheath perforations to penetrate the tissue. During one anchoring step in one anchoring location within the sheath (location in which the sheath is perforated), the interface is preferably kept stationary. Between successive anchoring steps in different anchoring locations within the sheath or within different sheaths, the interface is repositioned by moving the combination of vibrating element and counter element. Through the anchoring process, at least part of the sheath perforations and tissue regions which are situated adjacent to the perforations are penetrated or filled with the liquefiable material, which, on re-solidification of the liquefied material, retains the sheath in the tissue. After the anchoring process the vibrating element and the remains of the counter element (liquefiable material which was not liquefied and if applicable non-liquefiable parts of the counter element) are preferably removed from the anchored sheath, leaving the inner space of the anchored sheath substantially free from the liquefiable material.

The sheath has e.g. the form of a tube with round or non-round inner and outer cross sections (outer cross section=area enclosed by sheath circumference; inner cross section=cross section of inner space or channel), which are substantially the same along the sheath length. A proximal end of the sheath is open, a distal end of the sheath may be open or closed. At least distal regions of the vibrating element and the counter element are adapted to the inner cross section of the sheath but allowing substantially friction-free axial movement of these elements within the sheath. The one of the vibrating and counter element which reaches further distally comprises a proximal portion shaped to reach through at least a distal portion of the other element.

Preferably the counter element comprises an e.g. axial channel and the vibrating element comprises a shaft extending through this channel and being adapted to this channel for substantially friction-free axial movement of the two elements relative to each other.

As mentioned further above, the liquefiable material is preferably comprised by the counter element, which may consist entirely of this material or may comprise a portion made of this material which portion adjoins the interface with the vibrating element, whereas a second portion of the counter element, which is further removed from the interface with the vibrating element, may consist of a different material, which may not be liquefiable under the conditions of the anchoring process. It may be advantageous to design the counter element to comprise two separate parts, i.e. a liquefiable part which consists fully of the liquefiable material and a counter acting part serving for transmitting the force necessary for holding the liquefiable part against the vibrating element. Whereas at least a distal portion of the liquefiable part needs to be designed for being positioned in the sheath this is not a condition for the counter acting part.

In the preferred embodiment of the invention the vibrating element (e.g. sonotrode of an ultrasonic device) comprises a distal foot piece being adapted to the inner cross section of the sheath and a shall extending through the liquefiable part and the counteracting part of the counter element which both have the shape of a tube with an outer cross section (area enclosed by the outer tube circumference) being preferably about the same as the cross section of the foot piece, and an inner cross section (cross section of tube lumen) being adapted to the shaft of the vibrating element. The axial lengths of foot piece, liquefiable part and counter acting part together will in most cases, at least before the anchoring process, be larger than the axial extent of the perforated sheath and the counter acting part may comprise a proximal flange whose cross section is larger than the inner cross section of the sheath.

While the sheath remains in the tissue being anchored therein by regions of the liquefiable material extending through the sheath perforations into the surrounding tissue, the vibrating element, the remainder of the liquefiable part and the counter acting part are preferably removed from the sheath after the anchoring process.

The main advantages of device and method according to the first aspect of the invention are the following:

There is very little force (only hydraulic force of the flowing liquefied material) acting on the tissue in which the device is anchored, which renders the device applicable for anchorage in nearly any tissue.

There is very little force (only hydraulic force of the flowing liquefied material) acting on the sheath which is anchored in the tissue, such that the sheath may be made of a thin or flexible material.

The amount of liquefied material to be made to penetrate the tissue can be adapted, during the anchoring process, to the tissue encountered in an anchoring location.

The position of the sheath in the tissue can be determined fully independently of and before the anchoring process and it is fully independent of the amount of liquefiable material which is to penetrate the tissue for constituting a satisfactory anchorage.

A plurality of anchoring steps in a plurality of axially displaced anchoring locations in the same perforated sheath can be carried out in a fully independent manner. In particular, if necessary the tool can be re-charged with a fresh or additional liquefiable part between two such anchoring steps and there is no dependency between the amount of liquefied material used for the anchorage in one anchoring location and the axial distance of this anchoring location from a next anchoring location.

Instead of or in addition to anchorage in a plurality of anchoring locations in the same sheath, anchorage in different sheaths in a same operation site can be effected without removal of the distal end of the tool from the operation site.

The vibrating element and the counter element including the liquefiable material form a preassembled tool connected to a vibration source such that the surgeon needs to handle only the sheath and the tool.

After the anchoring process, the inner space of the sheath may be substantially free of the liquefiable material and may therewith be very suitable for further purposes, such as e.g. in-growth of tissue or fixation of further elements.

The device can be realized without the need of manufacturing elements consisting of a plurality of materials and the parts can be sterilized according to the material they are made of before assemblage of the tool.

As the sheath takes no part in the liquefaction it does not need to have a closed end, i.e. it may have a constant cross section over its full length, and it is therefore an item which is simple to be manufactured in a variety of differing axial lengths.

If the liquefiable material is comprised by the counter element the vibration characteristics of the vibrating element will hardly change during the anchoring process, even if a considerable part of the axial length of the liquefiable part is consumed. This means that the vibration source and the vibrating element can be tuned by the manufacturer to resonate such that e.g. maximum amplitude in axial direction occurs at the interface.

In the above and the following paragraphs, the invention is described as using mechanical vibration for activating the so called vibrating element for achieving liquefaction of the liquefiable material. Without departing from the basic idea of the invention it is possible to activate this element in other ways, e.g. by resistive or inductive heating, microwave, absorption of radiation etc. In such a case, the so called vibrating element becomes an active element The second aspect of the invention regards an improvement of the anchoring process based on specific guidance of the element comprising the liquefiable material.

The invention and a plurality of exemplary embodiments thereof are described in detail in connection with the following FIGS., wherein:

FIG. 2 shows anchorage of a plurality of sheaths which are connected or connectable to a plate;

FIG. 3 shows a further exemplary embodiment of the device according to the first aspect of the invention;

FIG. 4 shows a further exemplary embodiment of passage and shaft of vibrating and counter element;

FIGS. 16 and 17 show further features of the second aspect of the invention;

FIG. 18 illustrates device and method of the second aspect of the invention, wherein an element comprising the liquefiable material is anchored in a tissue opening.

FIG. 1 shows a preferred embodiment of the device according to the invention in five consecutive phases (a) to (e) of the anchoring method for establishing an anchorage in tissue using this device. The device comprises a tool 1 and a perforated sheath 2.

Figure 1:
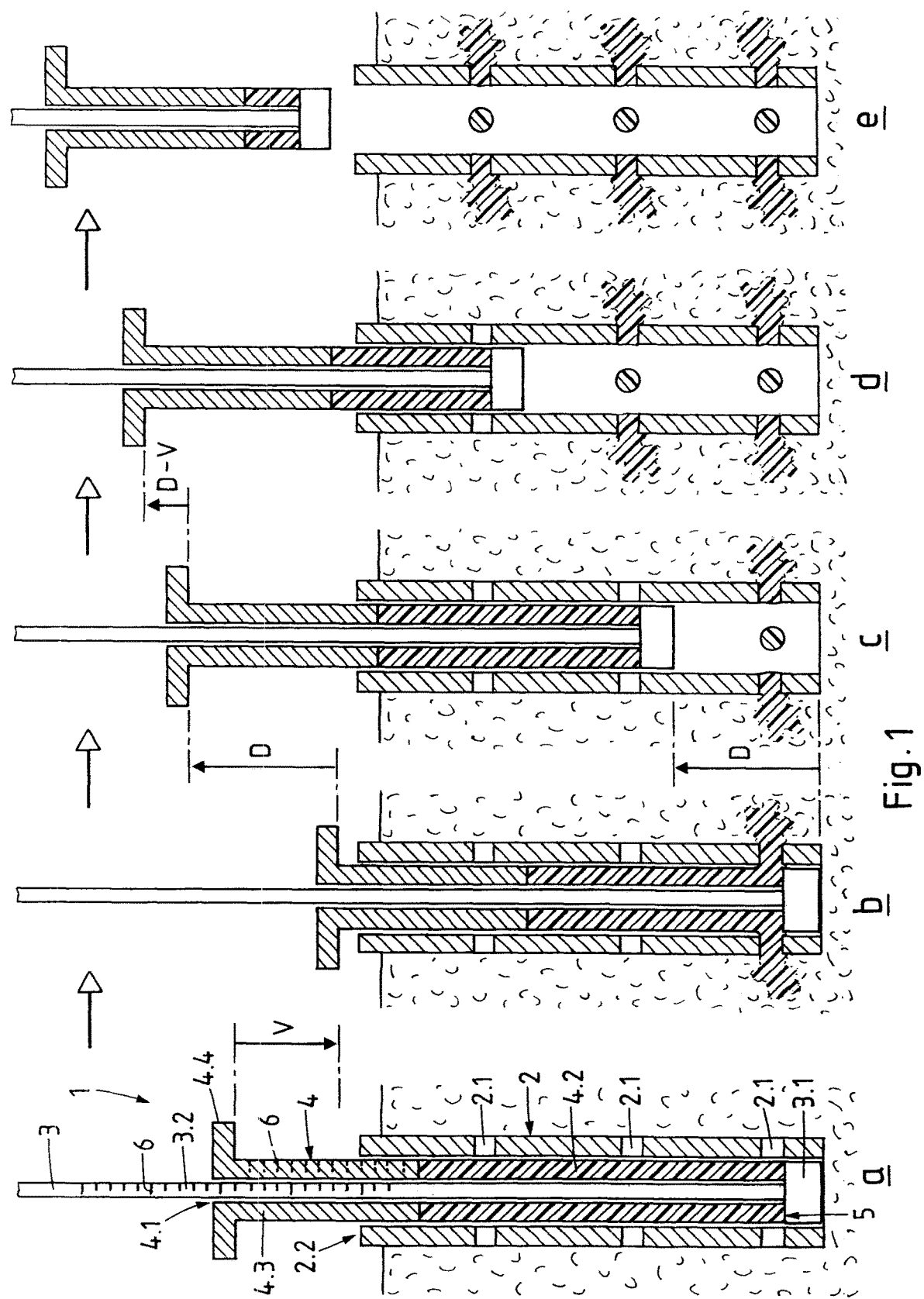
FIG. 1 shows five phases of an anchoring process according to the first aspect of the invention, in which anchoring process a perforated sheath is anchored in tissue in three axially spaced anchoring locations.

The perforated sheath 2 is generally tube-shaped and the sheath perforations 2.1 may be, as illustrated, discrete passages through the sheath wall but may also be sheath wall regions made of a porous material, e.g. of a sintered material or a foam material. The perforations are to provide passages through the sheath wall of which at least a part is to have diameters preferably not smaller than a few tenth of a millimeter, even more preferably not smaller than 0.3 mm. The sheath is open at its proximal end 2.2 and for the anchoring process is positioned in a tissue opening. For such positioning, the sheath may comprise a sharp or pointed distal end (not shown) and/or radially protruding and axially extending sharp edges (not shown). Such structures may also serve for the sheath to be held preliminarily (before the anchoring process) in the tissue opening. For the latter purpose the sheath may also comprise barbs or other retaining features on its outer surface or a collar on its proximal end making it suitable to be positioned and preliminarily held not only in a blind tissue opening but also in a tunnel reaching through the tissue.

The sheath material is preferably not liquefiable under the conditions of the anchoring process. It is e.g. a metal (e.g. titanium, titanium alloy, CoCr cast alloy), a ceramic material (e.g. aluminum oxide or zirconium oxide), a composite material (e.g. filled PEEK) or a high strength plastic material without filler (preferably a crystalline polymer having a glass transition temperature above 100° C. or a thermoset plastic material). If the sheath 2 is meant to remain in the tissue, the outer surface of the sheath 2, as a whole or in part, is preferably in a per se known manner equipped for enhancing integration in the tissue, e.g. for enhancing osseointegration. Alternatively, the sheath comprises a similar thermoplastic as the material to be liquefied, which can result in an additional welded connection between the anchoring material and the sheath material and/or in a deformation of the sheath and the perforations thereof.

The tool 1 comprises, in a preassembled configuration, a vibrating element 3 and a counter element 4 (including the liquefiable material) wherein for the anchoring process the tool is connected to a vibration source (not shown). Handling before anchorage and positioning of tool and sheath for anchorage can be carried out either independently (positioning sheath first and then tool in sheath) or together.

Both the vibrating element 3 and the counter element 4 have distal portions which are introduceable into the sheath 2 such that they touch each other at an interface 5, and which are axially moveable within the sheath 1. Both the vibrating element 3 and the counter element 4 comprise proximal portions reaching out of the proximal opening of the sheath, when the distal portions are introduced therein and serving for coupling the vibrating element to the vibration source and for coupling forces into the elements for holding them against each other at the interface 5.

In the preferred embodiment as illustrated in FIG. 1 the vibrating element 3 has a distal foot piece 3.1 and a shaft 3.2, wherein the foot piece and the shaft are connected with each other e.g. in a reversible manner, e.g. by being screwed together or by a press-fit, and wherein the shaft has a proximal end which is equipped for being coupled to the vibration source, again e.g. by screwing. Preferred materials for the vibrating element are metals, in particular titanium, titanium alloys, aluminum or stainless steel.

Advantageously the proximal face of the foot piece 3.1 which constitutes one part of the interface 5, is equipped such that it is not wetted by the liquefied material for not firmly adhering to the liquefiable part when the vibration is stopped. In particular for a liquefiable material having a relatively high melting temperature, it is advantageous to equip this proximal face of the foot piece with energy directors e.g. in the form of humps or ridges, in particular radially extending ridges which may further guide the liquefied material radially outwards, wherein the arrangement of such guide means for the liquefied material may be oriented towards perforated locations or openings of the sheath.

The counter element 4 comprises a passage 4.1 through which the shaft of the vibrating element extends and it consists of two separate parts, the liquefiable part 4.2 and the counter acting part 4.3. The liquefiable part is arranged between the foot piece 3.1 of the vibrating element 3 and the counter acting part 4.3. A proximal end of the counter acting part 4.3 may comprise a flange 4.4 having a cross section greater than the inner cross section of the sheath 2.

The liquefiable material of the liquefiable part 4.2 of the counter element 4 is chosen depending on the purpose of the anchorage. It is resorbable if the anchorage is to be subsequently fully replaced by a naturally grown connection (e.g. osseo-integration) between the tissue and the sheath, or if the sheath is to be removed later. It is non-resorbable for a permanent anchorage which is preferred in tissue which is not or hardly capable to form a naturally grown connection (e.g. osteoporotic bone tissue).

Suitable liquefiable materials for the liquefiable part 4.2 of the counter element 4 are e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel and Suk-Woo Haa, "Medizinaltechnik mit biokompatiblen Materialien and Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Höchst AG), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The thermoplastic materials may contain foreign phases or compounds serving further functions. In particular, the thermoplastic material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel).

Osseo-integration stimulating fillers that are only partially or hardly degradable, for non degradable polymers include: Bioglasses, Hydroxyapatite (>90% cristyllinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20.

Embodiments of bioactive fillers and their discussion can for example be found in X. Huang and X. Miao, J Biomater App. 2007 April; 21(4):351-74), J A Juhasz et al. Biomaterials, 2004 March; 25(6):949-55.

Particulate filler types include: coarse type: 5-20 μm (contents, preferentially 10-25% by volume), sub-micron (nanofillers as from precipitation, preferentially plate like aspect ratio >10, 10-50 nm, contents 0.5 to 5% by volume).

The material of the counter acting part 4.3 may or may not be liquefiable under the conditions of the anchoring process. The material of the counter acting part may e.g. be a material as above suggested for the vibrating element 3.

The shaft 3.2 of the vibrating element 3 and/or the counter acting part 4.3 of the counter element 4 may carry markings 6 for visual monitoring the relative movement of the vibrating element 3 and the counter element 4 relative to each other and/or the position of the interface 5 relative to the tissue surface (depth of the anchoring location in the tissue or in the sheath 2 respectively).

In phase (a) of the anchoring method as illustrated in FIG. 1, the sheath 2 is positioned in the tissue opening, wherein the tissue is dimensioned such that tissue walls adjoin the outer surface of the sheath closely (sheath substantially loose, push-fit, press-fit, screwed, etc.). The tissue opening is, as illustrated, e.g. a blind opening and the sheath is preliminarily held in its position by standing on the bottom of the opening. The distal portion of the pre-assembled tool 1 comprising the vibrating element 3 and, arranged on the shaft 3.2 of the latter, the liquefiable part 4.2 and the counter acting part 4.3 of the counter element 4 is introduced in the sheath 2 and the proximal tool end (shaft 3.2) is coupled to a vibrating source (not shown). The depth to which the tool 1 is introduced in the sheath 2 is adapted to the deepest perforation 2.1, i.e. the distal tool portion is introduced into the sheath such that the interface 5 between the vibrating element 3 and the counter element 4 is positioned in the area of this deepest perforation. The position of the interface 5 in the tissue opening or in the sheath 2 respectively can be visually monitored by comparing a mark (not shown) being stationary relative to the tissue surface with the markings 6 on the shaft 3.2. The same applies for later displacement (arrow D) of the interface 5 within the sheath 2 (phase (c)).

Phase (b) shows the end of a first anchoring step in which anchorage of the sheath 2 in the tissue is established through the deepest sheath perforations. During this anchoring step the vibrating element 3 and therewith the interface 5 is kept stationary relative to the sheath 2 and the counter acting part 4.3 is moved in a distal direction for keeping the liquefiable part 4.2 in contact with the foot piece 3.1 such enabling liquefaction at the interface 5 through which the axial length of the liquefiable part 4.2 is reduced. The travel of the counter acting part 4.3 relative to the tissue surface is indicated by the arrow designated with V. The size of V is determined by the amount of liquefied material which is desired or needed for achieving a satisfactory anchorage, which can be monitored e.g. by monitoring the force which is necessary for advancing the counter acting part at a constant power supplied by the vibrating source. The travel V can be monitored visually e.g. by monitoring the position of the proximal face of the counter acting part 4.3 relative to the markings 6 on the shaft 3.2 or by monitoring the markings 6 on the counter acting part 4.3 relative to the tissue surface. Of course it is possible also to monitor the amount of material simply by monitoring the time during which the vibration source is active.

Phase (c) shows the distal portion of the tool 1 being displaced such that the interface 5 is situated at a second anchoring location, wherein the displacement is carried out by displacing the tool 1, preferably the vibration source together with the tool, wherein the forces holding the liquefiable part 4.2 against the foot piece 3.1 being preferably maintained, but the vibration source preferably being switched off. The extent of the displacement (arrow D) coincides substantially with the axial distance between the two anchoring locations. Experiments show that such displacement is easily achieved if the vibration is stopped immediately before the displacement. If the vibration is stopped longer before the displacement, the liquefied material is solid again and the liquefiable part 4.2 is rigidly connected with the anchoring produced beforehand. For making the displacement possible without damaging the anchorage, this connection needs to be loosened by a short (0.5 to 3 seconds) switching on of the vibration source. The anchorage procedure at the second anchoring location is the same as the anchorage procedure at the first anchoring location (phase (a)).

Phase (d) shows the interface 5 being positioned at a third anchoring location ready for a third anchoring process and phase (e) shows the tool 1 removed from the sheath 2 after the anchoring step at the third anchoring location. For further anchoring processes, the tool is recharged by exchanging the remaining liquefiable part with a new one or by adding a new liquefiable part to the remaining one. The recharging is e.g. carried out by removing the foot piece 3.1 from the shaft 3.2, by pushing the new liquefiable part onto the shaft and by reattaching the foot piece on the shaft (for other recharging methods, see FIG. 8).

In the process as shown in FIG. 1, nearly the whole liquefiable part 4.2 has been used up in the three anchoring steps and a small rest thereof is removed from the sheath 2. Obviously it is advantageous to provide a liquefiable part 4.2 having an axial length such that it comprises enough liquefiable material for all anchoring steps at least in one sheath. However, if the liquefiable part proves to have been too short, removal of the tool 1 from the sheath 2 and recharging of the tool between e.g. the second and the third anchoring step does not change the anchoring result.

Figure 7:
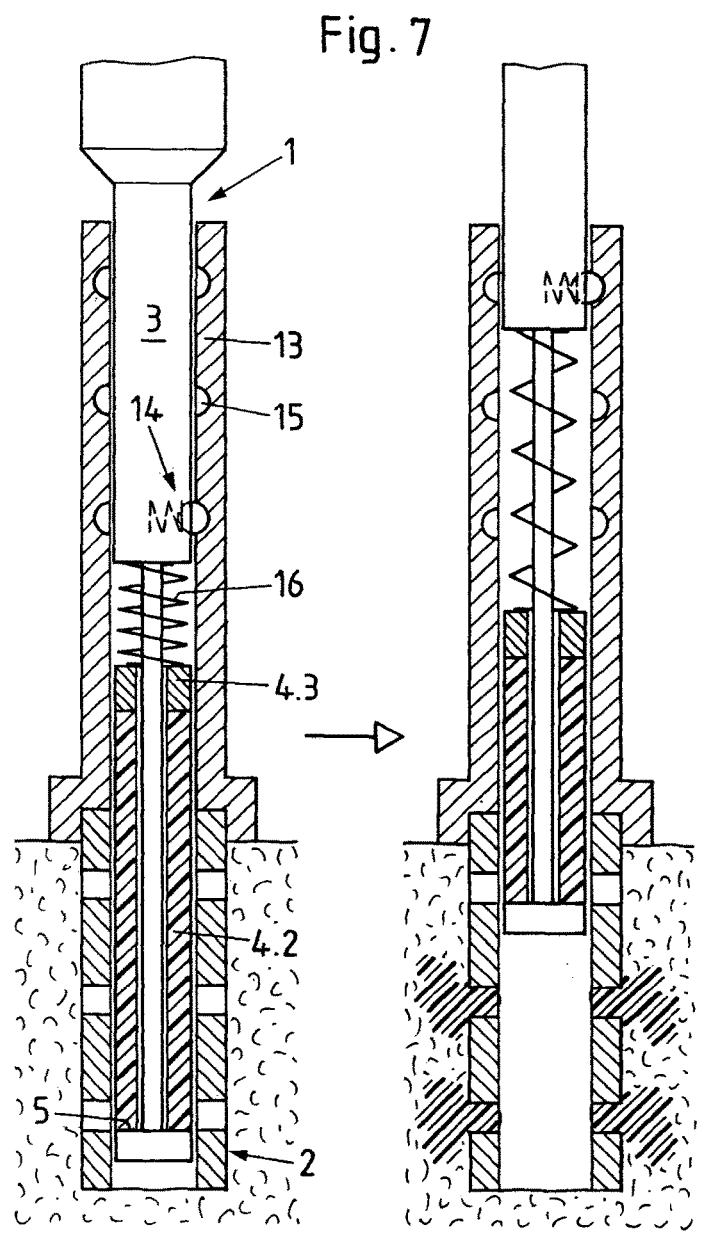
FIG. 7 shows further features of the tool suitable for the anchoring process as illustrated in FIG. 1.

For the device as illustrated in FIG. 1 it is the surgeon or other operator who guides the tool 1 relative to the sheath 2 and the movement of the counter acting part 4.3 relative to the vibrating element 3 and who applies the forces necessary for holding the foot piece 3.1 of the vibrating element 3 against the liquefiable part 4.2 for enabling liquefaction. Therein he preferably holds the shaft 3.2 of the vibrating element 3 or the vibration source respectively with one hand and uses the other hand for pushing the flange 4.4 of the counter acting part 4.3 against the tissue surface. However, it is possible also to provide biasing means between the counter acting part 4.3 and a housing of the vibration source which bias the counter element 4 against the foot piece 3.1 and move the counter acting part 4.3 relative to the vibrating element 3 such that the surgeon or other operator only needs to guide the tool 1 relative to the sheath 2. Tools comprising the named biasing means are e.g. described in the U.S. application No. 61/033,066, the contents of which is herein disclosed by reference. An example of a suitable biasing means for the tool as illustrated in FIG. 1 is shown in FIG. 7.

When the sheath 2 is anchored securely in the tissue a further element (not shown) can be mounted on the proximal sheath end for which purpose this sheath end may be equipped e.g. with an inner thread cooperating with an outer thread of such further element or with a part of a snap-connection. Depending on the size and shape of the sheath 2 and on the site in which it has been anchored, the further element may comprise e.g. an eyelet threaded onto a suture or wire or it may constitute an artificial joint part (joint ball or socket) or a drug delivery element. The further element may also constitute a head for the sheath 2, wherein the head either has a shaft which is driven through a soft tissue or further implant part before being fastened in the proximal end of the anchored sheath 2, or wherein the proximal sheath end protrudes from the tissue and is driven through the soft tissue or further implant part before the head is fastened therein. The sheath 2 may also constitute a dental implant wherein the further implant part is e.g. an abutment or a crown. If the sheath 2 as shown in FIG. 1 comprises a plurality of anchoring locations it is particularly suited for applications in which a great axial sheath length is required. Exemplary such applications in which according to the state of the art long screws such as trochanter screws or pedicle screws are used, wherein a plate (e.g. a trochanter plate) or a rod (e.g. a vertebral fixation rod) may be attached to the proximal sheath end.

Device and method as shown in FIG. 1 may be altered e.g. in the following manner without departing from the scope of the invention, wherein the listed alterations may also be combined with each other without departing from the scope of the invention:

- Only two or more than three anchoring locations are provided in the sheath.
- Each anchoring location is constituted by a freely selectable number of openings, wherein a plurality of such openings may comprise openings of differing sizes and forms and may be spaced around the circumference of the sheath in a regular or an irregular pattern.
- Three or more than three anchoring locations are arranged on the sheath with differing axial distances from each other.
- Each one of the anchoring locations extends over a larger axial portion of the sheath (e.g. axially extending slits as sheath perforations) and during each anchoring step the interface 5 or the vibrating element 3 respectively is axially moved to ensure anchorage over the whole anchoring location.
- The sheath is positioned such that, in the anchoring location, there is a space between the sheath and the tissue, wherein at least part of the liquefied material re-solidifies in this space.
- The sheath has an outer cross section that is fully independent from the inner cross section.
- The sheath has more than one inner spaces or axial channels which may have differing depths.
- Instead of comprising two separate parts (liquefiable part 4.2 and counter acting part 4.3), the counter element 4 is a one part element constituted by the liquefiable part and the counteracting part being fixed together or by fully consisting of the liquefiable material. The disadvantage of such embodiments are the facts that either the exchange of the liquefiable part 4.2 is more complicated or only a smaller portion of the liquefiable material can be used for the anchorage.
- The liquefiable part 4.2 is constituted by a plurality of bead-like items being threaded onto the shaft 3.2. The advantage of such embodiments is the fact that the amount of liquefiable material can be easily replenished or adapted for different anchoring processes.
- The liquefiable part 4.2 is not a part of the counter element 4 but it is a part of the vibrating element 3, i.e. it is fixedly mounted on the foot piece 3.1 or shaft 3.2 of the vibrating element 3, such that the interface at which liquefaction occurs is situated between the liquefiable part 4.2 and the counteracting part 4.3. The disadvantages of such embodiments are the facts that the vibration characteristics of the vibrating element (including the liquefiable material) change during the anchoring process which may make continuous tuning necessary, that less of the vibration energy can be transmitted to the interface (damping effect of the thermoplastic material), that, for maintaining the interface stationary relative to the sheath, the vibrating element and therewith the vibration source need to be moved, and that, for the case of the sheath 2 being positioned in a blind opening, the deepest anchoring location cannot be very near the bottom of the opening.
- The function of the vibrating element 3 and the counter element 4 are exchanged, i.e. the vibration source is coupled to the element 4 (up to here called counter element). The disadvantage of such embodiments is the fact that the shaft 3.2 needs to exit from a passage in the element 4 and therefore needs to be bendable or flexible (see FIG. 3).
- The sheath 2 is not positioned in a blind bore provided in the tissue but in a tunnel leading through the tissue. The disadvantage of such embodiments is the fact that the sheath 2 needs to comprise means for being preliminarily held in the tissue opening. Such means may be barbs or other retention means or a proximal flange. Furthermore, the sheath 2 can be preliminarily held in the opening by friction (press-fit).
- The sheath 2 is not a rigid item but is made of the flexible material such as a tube consisting of woven or knitted metal wire, of a fibrous or non woven material, or of a perforated flexible foil.
- The outer surface of the sheath 2 has not a constant cross section over its length but e.g. tapers from a proximal end to a distal end to form a steep cone which is preferably introduced in a correspondingly tapering tissue opening.
- The inner space of the sheath 2 has a stepped form, wherein the cross section of this inner space gets smaller from the proximal sheath end to the distal sheath end. At least one anchoring location is situated in each sheath section between steps and anchorage at the anchoring locations are accomplished by using different tools 1 of different distal cross sections. The disadvantage of such embodiments is the need of different tools, the advantage is the fact that in particular conical sheaths can be anchored in the same manner (e.g. shaft for hip prosthesis).
- The sheath is pushed over the distal end of the tool (push-fit) and sheath and tool are positioned in the tissue opening together.
- For guiding and counteracting deformation of a liquefiable part which protrudes at least temporarily from the sheath, an outer guide tube lengthening the sheath in a proximal direction is provided (see FIGS. 7 and 13).

FIG. 2 shows a further embodiment of the invention wherein the tool 1 comprising the vibrating element 3, the counter element 4 and the liquefiable material is substantially the same as the tool shown in FIG. 1. The device comprises in addition to the tool 1 a plurality of perforated sheaths 2 and 2' which are associated with an implant by e.g. being part thereof (sheaths 2). According to FIG. 2 the sheaths 2 protrude from a plate 10 as e.g. used in osteosynthesis or from a flattish resurfacing implant. The sheaths 2 are positioned in corresponding openings provided in the tissue or may be simply driven into this tissue which may be bone tissue of a reduced mechanical stability (osteoporotic bone tissue). The sheaths 2 and therewith the plate 10 or implant are anchored in the tissue by using the tool 1, wherein the sheaths 2 are anchored in at least one anchoring location and the same tool is used for anchoring all sheaths 2 and 2'.

It is possible also to provide the plate 10 or implant separate from the sheaths as shown for sheath 2' and to connect the two e.g. by providing the plate 10 with a suitable structure (cavities, rough surface, thread etc.) on the wall of a through opening for the sheath or with a porous insert in the region of this through opening, by providing the sheath 2' with a perforation 2.1' near its proximal end and by using the contact between the sheath end and the plate as further anchoring location, wherein anchorage in this anchoring location results in a firm connection between the plate 10 and the sheath 2 possibly in combination with an anchoring in the tissue.

FIG. 3 shows a further embodiment of the device 1 according to the invention. The device again comprises a tool 1 and a sheath 2, the tool 1 comprising a vibrating element 3 and a counter element 4 being in contact with each other at an interface 5. Other than according to the embodiment according to FIG. 1, the sheath 2 comprises a proximal collar or flange 2.2 for being held in the tissue opening which may be a tunnel, and the perforation 2.1 is constituted by a ring (or otherwise shaped wall portion) of a porous material (e.g. sintered material or ceramic or metal foam). It is of course possible also to provide a sheath which is fully made of a porous material and to use this porosity in the sense of a perforation for the anchorage process only at specific locations. Other than in the embodiment according to FIG. 1 the counter element 4 reaches further distal than the vibrating element 3 and therefore a distal portion of the vibrating element 3 comprises a passage 3.3 through which flexible shafts 4.5 (e.g. wires or ribbons) of the counter element 4 reach to exit from the vibrating element further proximal. The distal portion of the counter element comprises the liquefiable material, the flexible shafts being e.g. molded into the Liquefiable material.

For the anchoring process, the distal end of the tool 1 is inserted in the sheath 2 as shown in FIG. 3, the vibrating element 3 being connected to the vibration source (not shown). The vibrating element 3 and counter element 4 are held against each other by forcing the vibrating element or the vibration source respectively in a direction against the tissue and counteracting this forcing by pulling on the shafts 4.5 of the counter element 4 in an opposite direction. For visual monitoring of the amount of material being liquefied and of the position of the interface 5 within the sheath, the vibrating element 3 and the shafts 4.5 may be equipped with markings 6.

FIG. 4 is a cross section in the region of passage and shafts through a further embodiment of vibrating element 3 and counter element 4 which may be advantageous for an embodiment of the device according to the invention as shown in FIG. 3 but is, with reversed functions, also applicable for the embodiment according to FIG. 1. In this embodiment the passage is not a central channel as shown in FIGS. 1 and 3 but a plurality of grooves 20 running in axial direction along the outer surface of the more proximal element (counter element 4 according to FIG. 1, vibrating element 3 according to FIG. 3) and the other element (vibrating element 3 according to FIG. 1 and counter element 4 according to FIG. 3) comprises a plurality of shafts 21 extending in the grooves 20, wherein the shafts 21 may be flexible or rigid, depending on the means with which the forces for holding the elements against each other are coupled into the elements.

Figure 5:
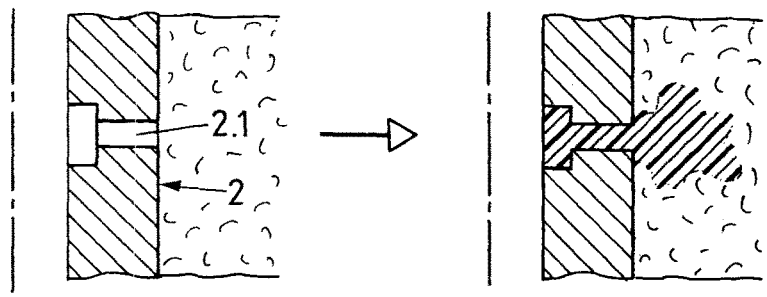
FIG. 5 shows a further embodiment of a sheath perforation.

FIG. 5 shows a detail of the sheath perforation 2.1 of the device according to the invention (left hand side of FIG. 5) and of the anchorage being established with this sheath 2 and the method according to the invention (right hand side of FIG. 5). Other than shown in the previous FIGS. the perforation 2.1 through the wall of the sheath 2 is neither constituted by openings of substantially constant cross section nor by a porous wall section but it is an opening with an enlarged mouth on the inside of the sheath which allows the anchorage to have a countersunk head on the inside of the sheath.

Figure 6:
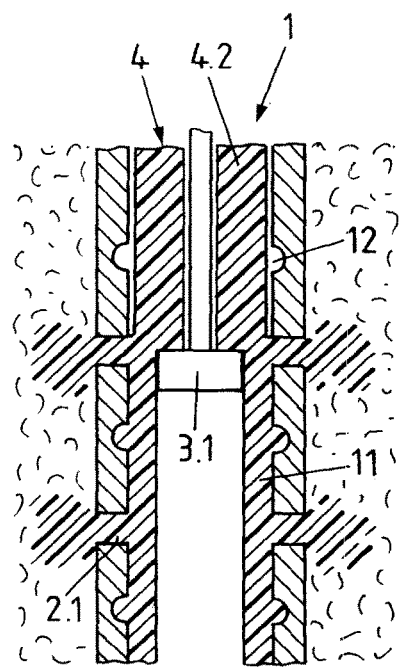
FIG. 6 shows a further embodiment of the anchoring process as shown in FIG. 1.

FIG. 6 illustrates a further embodiment of device and method as already illustrated in FIG. 1. In contrast to the latter, the cross section of the foot piece 3.1 of vibrating element 3, or possibly of the distal end of the tool 1 inclusive the liquefiable part, is smaller than the inner cross section of the sheath 2 and is therefore not able to keep the channel of the sheath 2 free of liquefied material. As a result, there remains a layer 11 of the liquefiable material on the walls of this inner channel, wherein this layer interconnects the anchorages in neighboring anchorage locations and may further serve as re-enforcement of the sheath 2 or means for connecting separate sheath sections. In the latter case, the sheath as shown in FIG. 6 is e.g. sectioned in at least one of the anchoring locations with perforations 2.1 and the inner wall of the sheath segments is preferably equipped with at least a rough surface or with cavities or grooves 12, which are filled with the liquefied material during the anchoring process and constitute a positive fit connection between the layer 11 and the sheath and therewith between the sheath segments. Application of a segmented sheath is particularly advantageous in operations in which introduction of longer sheaths necessitates removal of a larger amount of tissue as is e.g. the case with for the introduction of a rod into the marrow space of a long bone through a lateral opening in the bone.

Experiments show that radial play between the distal cross section of the tool 1 and the inner cross section of the sheath 2 of about 0.05 mm will leave the channel in the sheath substantially free of the liquefiable material as illustrated in FIG. 1. Larger play will result in the layer 11 of the liquefiable material as shown in FIG. 6.

FIG. 7 shows further features which may be added to device and method as illustrated in FIG. 1 and of which at least a part has been mentioned already further above. The principle of the device and the method remain the same and same elements are denominated with same reference numerals. The device again comprises a tool 1 and a sheath 2 and the method serves for anchoring the sheath in a tissue opening, wherein, on the left hand side of FIG. 7, the device is shown with the tool 1 introduced in the sheath 2 ready for the first anchoring step, and on the right hand side after completion of two anchoring steps in two anchoring locations, the tool being positioned in the sheath ready for a third anchoring step.

The device comprises in addition to the device shown in FIG. 1 a guide tube 13 which constitutes a removable axial sheath extension extending from the proximal end of the sheath 2. This guide tube, which is e.g. screwed or snapped onto the proximal sheath end may serve varying purposes which are discussed in the following paragraphs.

The guide tube 13 may simply serve for restricting deformation of a proximal end of the liquefiable part 4.2 at its interface with the counteracting part 4.3 which may occur when this interface is located outside the sheath 2 and which may prevent introduction of this interface into the sheath at a later stage of the anchoring process.

The guide tube 13 and a proximal region of the vibrating element my further comprise means which enable the operator to accurately position the tool for subsequent anchoring steps without the necessity of visual monitoring or corresponding markings on tool and/or sheath. These means comprise e.g. a spring and ball arrangement 14 (undercut recess containing ball and spring, the spring resiliently forcing the ball towards the recess mouth) on the vibrating element 3 and a plurality of corresponding grooves 15 in the guide tube 13 (or vice versa), wherein the axial distances between the grooves 14 are the same as the axial distances between the anchoring locations of the sheath 2. The grooves 15 are dimensioned to leave play between groove and ball such that the vibration of the vibrating element 3 is not obstructed. Between successive anchoring steps, the vibrating element 3 is moved relative to the guide tube 13, or relative to the sheath 2 respectively, such that the ball of the ball and spring arrangement 14 is forced out of one groove 15 to come to rest in a neighboring groove 15.

The guide tube 13 may further serve for guiding a resilient means (e.g. spring 16) acting between the vibrating element 3 and the counter element such that the distal face of the liquefiable part 4.2 is held against the proximal face of the foot piece 3.1 and that the liquefiable part is advanced for compensating the liquefied material flowing from the interface 5 during the anchorage process. This means that in the embodiment according to FIG. 7, spring 16 takes over part of the function of the operator as described in connection with FIG. 1. The embodiment comprising the spring 16 is possible also without the guide tube 13, wherein the spring may be positioned within the sheath 2 during the whole anchoring process or during at least part thereof. In the latter case the condition regarding the dependence of the axial lengths of the counter element and the sheath as given for the embodiment according to FIG. 1 is not relevant.

The tool which is used in an anchoring process as illustrated in FIG. 1 is not only suitable but may also be used for supplying a material having thermoplastic properties and being liquefiable by mechanical vibration to an operating site. The material my serve in the operating site as a joining interface or space filler between tissue parts, between a tissue part and an artificial element or between two artificial elements. Such material supply is specifically advantageous for operating sites with difficult access and/or for minimally invasive surgery.

Figure 8:
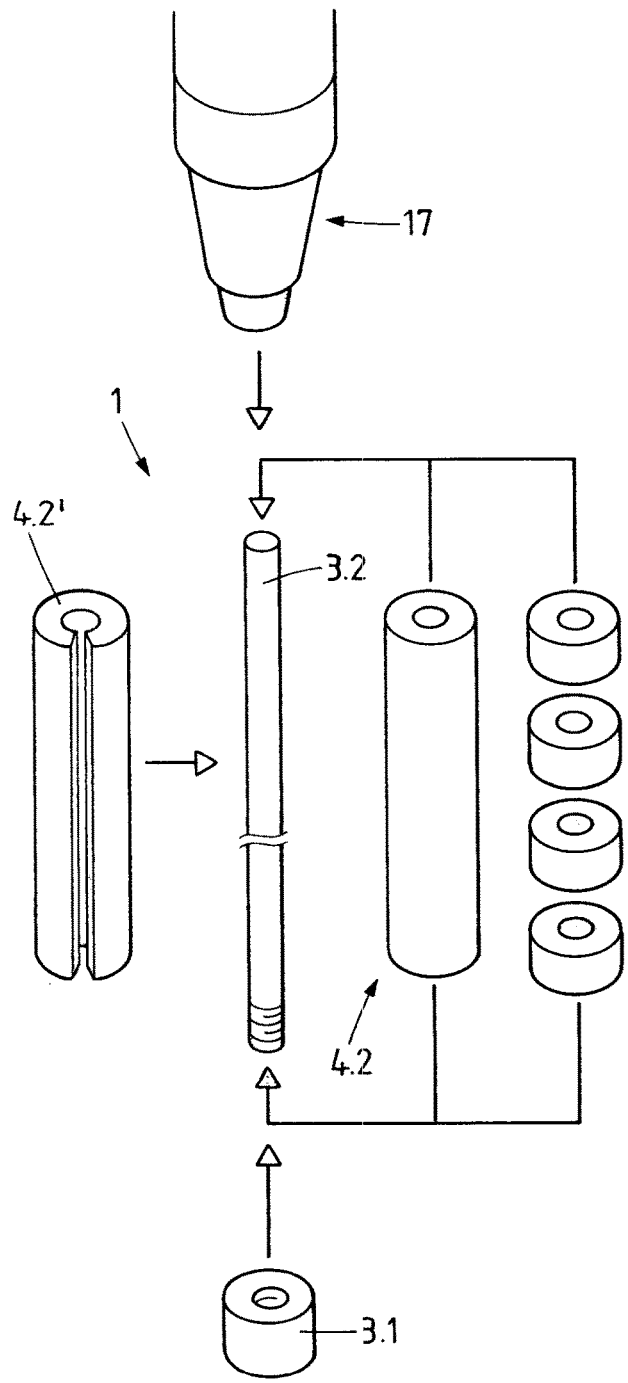
FIG. 8 illustrates the re-charging of the device as shown in FIG. 1.

FIG. 8 illustrates in a very schematic manner charging or re-charging of the tool 1 with liquefiable parts 4.2 or 4.2', wherein three ways for such charging or re-charging are illustrated. If the shaft 3.2 of the vibrating element is removably connected with the foot piece 3.1, recharging is e.g. effected by removing the foot piece 3.1 from the shaft, by pushing at least one liquefiable part 4.2 (tube, tubes or beads) in an axial direction onto the shaft and by subsequent re-attaching the foot piece 3.1 to the shaft 3.2. If the shaft is removably coupled to the vibration source, e.g. with the aid of a chuck 17, the shaft is removed and the at least one liquefiable part is pushed onto the shaft in an axial direction. The third illustrated way for charging or recharging the tool 1 with at least one liquefiable part does not necessitate removability of the foot piece 3.1 from the shaft 3.2 nor of the shaft 3.2 from the vibration source but it necessitates lengthwise slotted liquefiable parts 4.2'. Such liquefiable parts 4.2' (one slotted tube, a plurality of slotted tubes or a plurality of slotted beads) are capable of being pushed in a radial direction onto the shaft, wherein the shaft is pushed through the slot which necessitates a corresponding elasticity of the liquefiable material. Furthermore it is possible to design the liquefiable part a spirally item and to "screw" it onto the vibrating element, wherein neither removal of the foot piece nor uncoupling of the shaft is necessary.

Figure 9A:
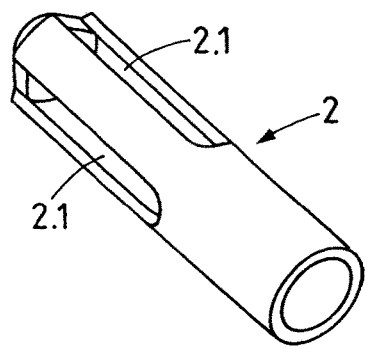
FIGS. 9A, 9B and 10 show further exemplary embodiments of sheaths suitable for the methods according to the invention.
Figure 9B:
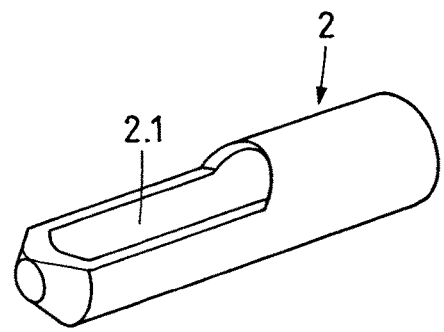

FIGS. 9A, 9B show further exemplary embodiments of sheaths 2, which differ from the sheaths shown in the previously discussed FIGS. in particular regarding the arrangement of the perforations 2.1. FIG. 9A shows a sheath 2 with one only anchorage location, wherein the corresponding perforations have the form of axially extending slits (e.g. three such slits). FIG. 9B shows a sheath with one only anchorage location which comprises one only slit, enabling anchorage in one selected radial region. For guiding the supply of liquefied material to this selected radial region it is advantageous to equip the proximal face of the foot piece of the used tool (not shown) with at least one radially running groove as previously mentioned, wherein the groove or groove pattern is restricted to one radial region and wherein suitable means are provided for aligning the groove or groove pattern of the foot piece with the perforation of the sheath. The sheath 2 according to FIG. 9B is particularly suited for fixing an intervertebral prosthesis or plate in the bone tissue of the vertebral bodies wherein the one opening 2.1 is made to face (relative to the vertebral column) upwards or downwards respectively.

Figure 10:
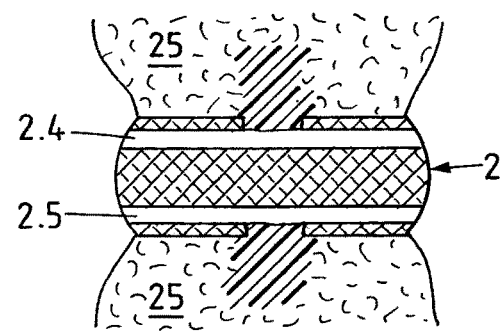

FIG. 10 shows a further example of a sheath suitable for the anchoring process as illustrated in FIG. 1. This sheath 2 differs from the previously discussed sheaths in that its outer cross section is fully independent from the cross section of its inner space and that it comprises more than one such inner spaces designed for successive anchoring processes using the same tool. These inner spaces are e.g. two channels 2.4 and 2.5 or even four such channels. Such a sheath is e.g. as illustrated in FIG. 10 an element or cage to be positioned in the intervertebral space between two neighboring vertebral bodies 25, wherein the intervertebral space constitutes the tissue opening being provided for positioning the sheath. One channel 2.4 or two laterally spaced such channels are arranged in an upper section of the cage and their perforation or perforations are facing towards the upper one of the vertebral bodies 25. One channel 2.5 or two laterally spaced such channels are arranged in a lower section of the cage and their perforations are facing towards the lower vertebral body. The cage is anchored by introducing a tool e.g. as shown in FIG. 1 into each one of the channels 2.4 and 2.5 in succession and therewith providing a plurality of anchoring locations as illustrated in FIG. 10.

In a similar way as illustrated in FIG. 10 it is possible to anchor other load-bearing implants in bone tissue, such as e.g. endoprostheses replacing joint parts (hip, knee, shoulder, etc.), implants for replacing an intervertebral disk or nucleus, spacer implants for vertebroplasty, trauma implants such as intramedullary nails, soft tissue fasteners or suture retainers, and so on. Site for such anchoring is in particular cancellous bone of the epiphysal and metaphysal bone areas. However, in cases such as e.g. fixation of an intermedullary nail or of the distal part of a hip joint replacement prosthesis, it is possible also to make the liquefied material to flow into an empty space between tissue and implant.

Furthermore, the device and method according to the invention can also be applied for in situ anchoring of one implant part in another implant part. Examples of such applications are e.g. described in the publication WO2008/034276.

Figures 11, 14:
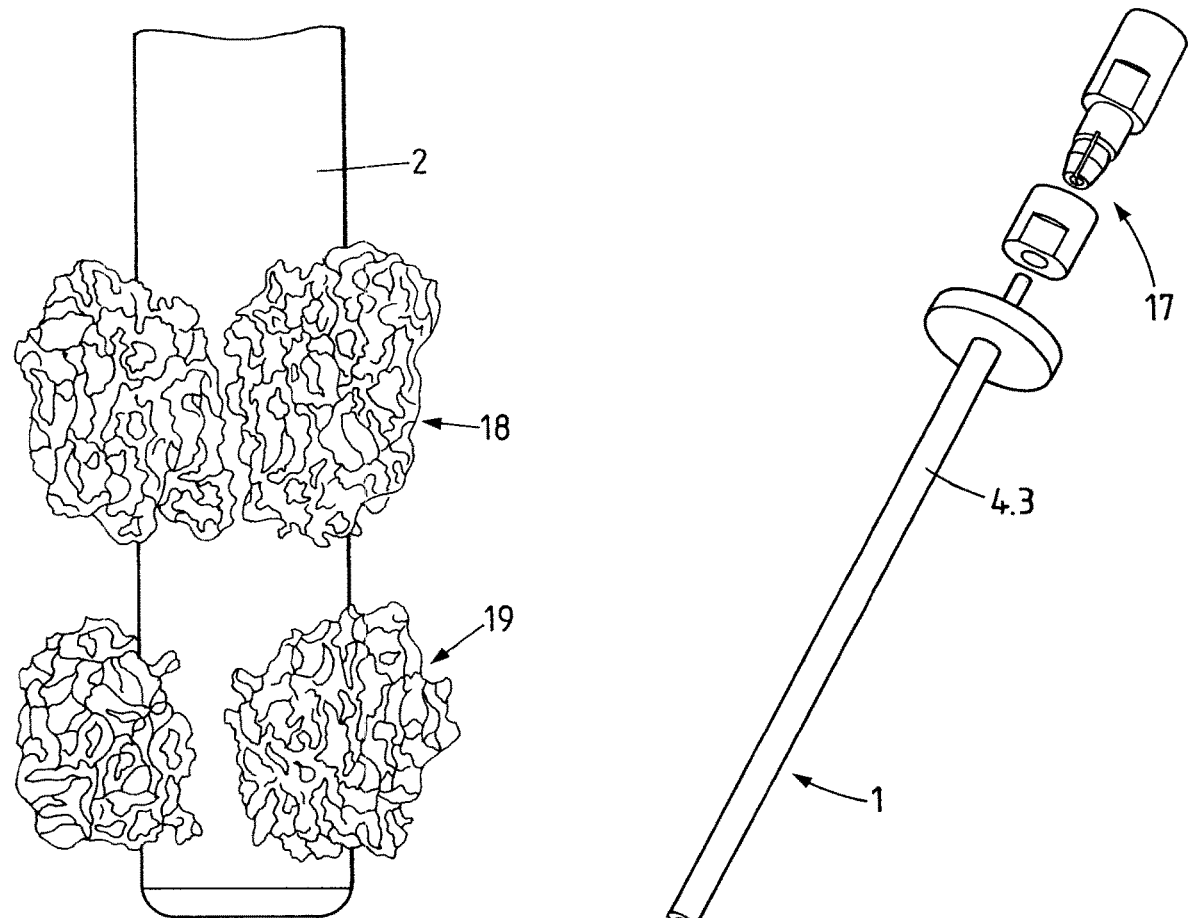
FIG. 11 is a photograph of an experimental anchoring effected with the aid of the method as illustrated in FIG. 1.
FIGS. 12 to 14 illustrate the anchoring process as shown in FIG. 1 in an application in which the sheath is a cannulated pedicle screw.

FIG. 11 shows the anchorage achieved in an experiment in which a sheath 2 (only partly visible) similar to the sheath shown e.g. in FIG. 1 and comprising two axially spaced anchorage locations 18 and 19 is anchored in the bone model material available under the trade name "Sawbones" with the aid of a liquefiable part consisting of PLA. For preparing the photograph the saw bone was removed after the anchorage process. The sheath 2 having round cross sections has an outer diameter of e.g. 4 to 8 mm and an inner diameter of e.g. 2 to 5 mm. The anchorage process is carried out using ultrasonic vibration of e.g. a 20 to 40 kHz frequency and a 10 to 70 μm (peak to peak) longitudinal amplitude at the foot piece. The force exerted on the counter acting piece is in the region of 20 to 100 N and for each anchoring step an anchoring time of between about 1 and 10 s is suitable. FIG. 11 shows clearly the way in which the liquefiable material which during the anchoring process was liquefied and made to flow through the sheath perforations and to penetrate the saw bone has adapted the structure of the saw bone to form therewith a tight positive fit connection.

Figure 12:
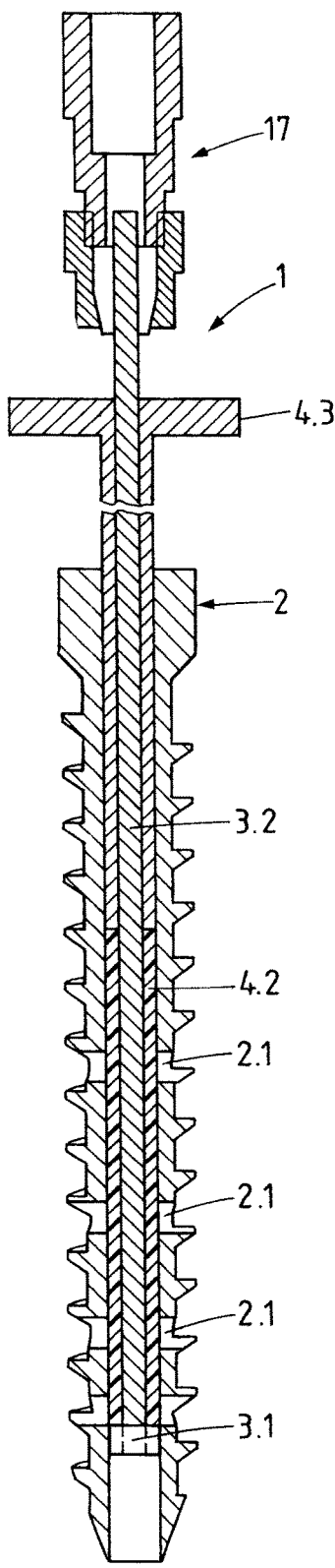
Figure 13:
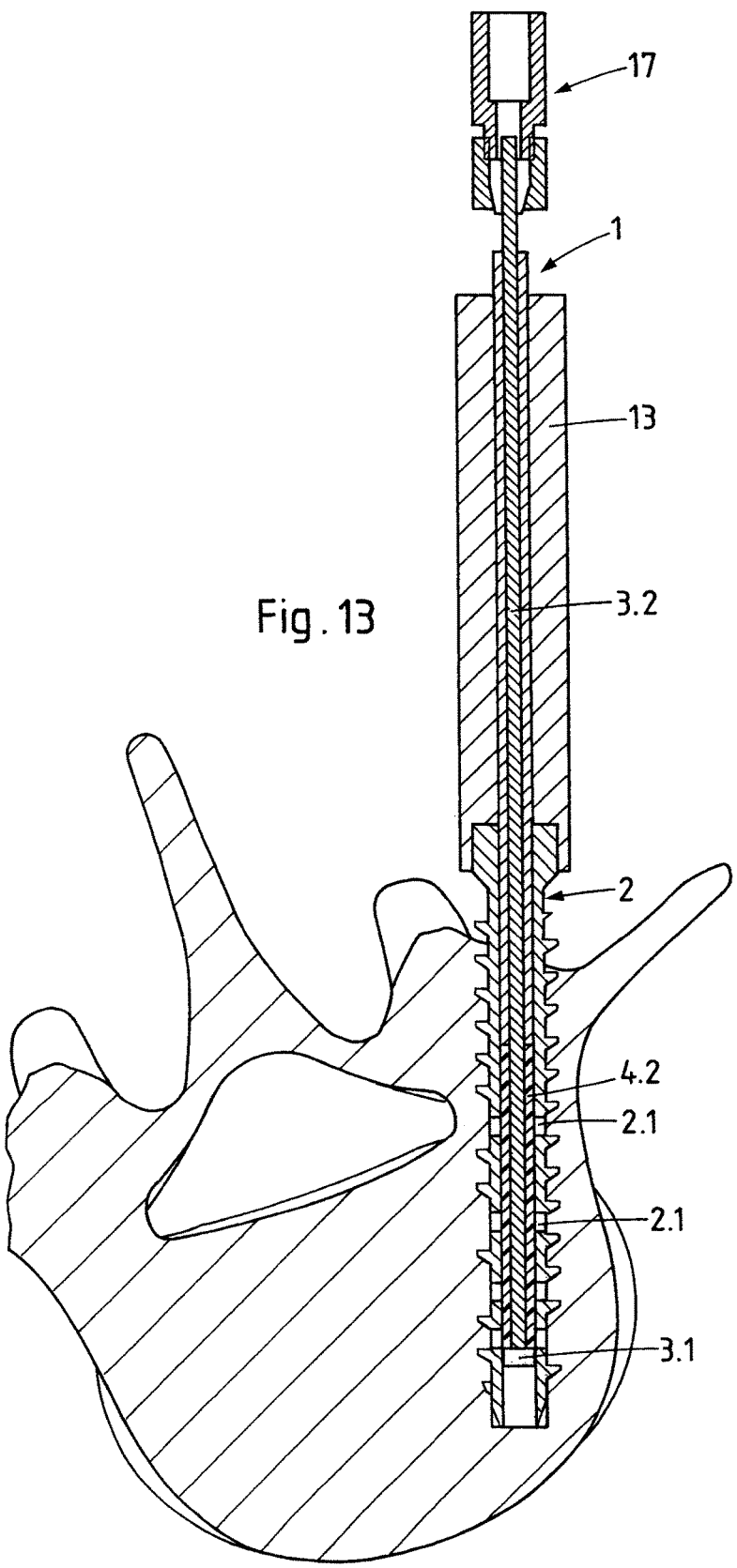

FIGS. 12 to 14 illustrate a further advantageous application of device and method as illustrated in the previously discussed FIGS. This application regards a per se known cannulated screw (pedicle screw) which constitutes the sheath 2 of the inventive device as discussed above. With the aid of an anchorage process according to the invention, the pedicle screw, which is screwed into the vertebral body in a per se known manner is further secured in the vertebral body and the bone tissue of this vertebral body is strengthened or augmented by the liquefiable material. FIGS. 12 and 13 show axial sections through sheath 2 and tool 1 which are ready for the anchoring process. FIG. 13 shows in addition the vertebra in which the pedicle screw is to be fixed and a guide tube 13 as previously discussed in connection with FIG. 7. FIG. 14 is an exploded illustration of sheath 2 and tool 1. FIGS. 12 to 14 show embodiments of all device parts which are suitable for the specific application and whose function in the anchorage process have been discussed in connection with the previous FIGS. These parts are in particular: sheath 2 comprising perforations 2.1 in axially distanced anchorage locations and tool 1 comprising the vibrating element 3 with the shaft 3.1 and the foot piece 3.2 and being coupled to the vibration source with the aid of chuck 17, and the counter element 4 with the liquefiable part 4.2 and the counteracting part 4.3.

The sheath is e.g. a cannulated and fenestrated pedicle screw available under the trade name "CD-Horizon" and having an axial channel with a diameter of 2 mm. The shaft 3.2 of the vibrating element has a diameter of 0.8 mm (e.g. titanium wire) and an axial length of ca. 100 mm. The liquefiable part 4.2 has an outer diameter of 2 mm and an axial length of e.g. 30 mm and consists of PLA. The used ultrasonic device has a max. power consumption of 80 W and a vibration frequency of 30 KHz with a vibration amplitude (peak to peak) of about 20 µm at the foot piece. Anchorage is accomplished in a time of not more than 10 s per anchorage location with an axial force in the region of 50 N. Experiments using the named pedicle screw and "Sawbones 7.5Pcs" (trade name) and comparing the screw being screwed into the Sawbones with and without additional anchoring showed that the additional anchoring was able to increase the pull-out force by 50 to 100%.

FIGS. 15 to 18 illustrate the second aspect of the invention, wherein the idea of the tube-shaped liquefiable part of the first aspect of the invention is further developed and adapted to further applications. The basis of this second aspect is again anchorage in tissue with the aid of mechanical vibration, in particular ultrasonic vibration, and a thermoplastic material which is liquefiable by the mechanical vibration. The above disclosure in particular regarding this anchorage principle, the materials which are suitable for such anchorage, and the varying embodiments of the sheath are valid for the second aspect of the invention also.

Figure 15:
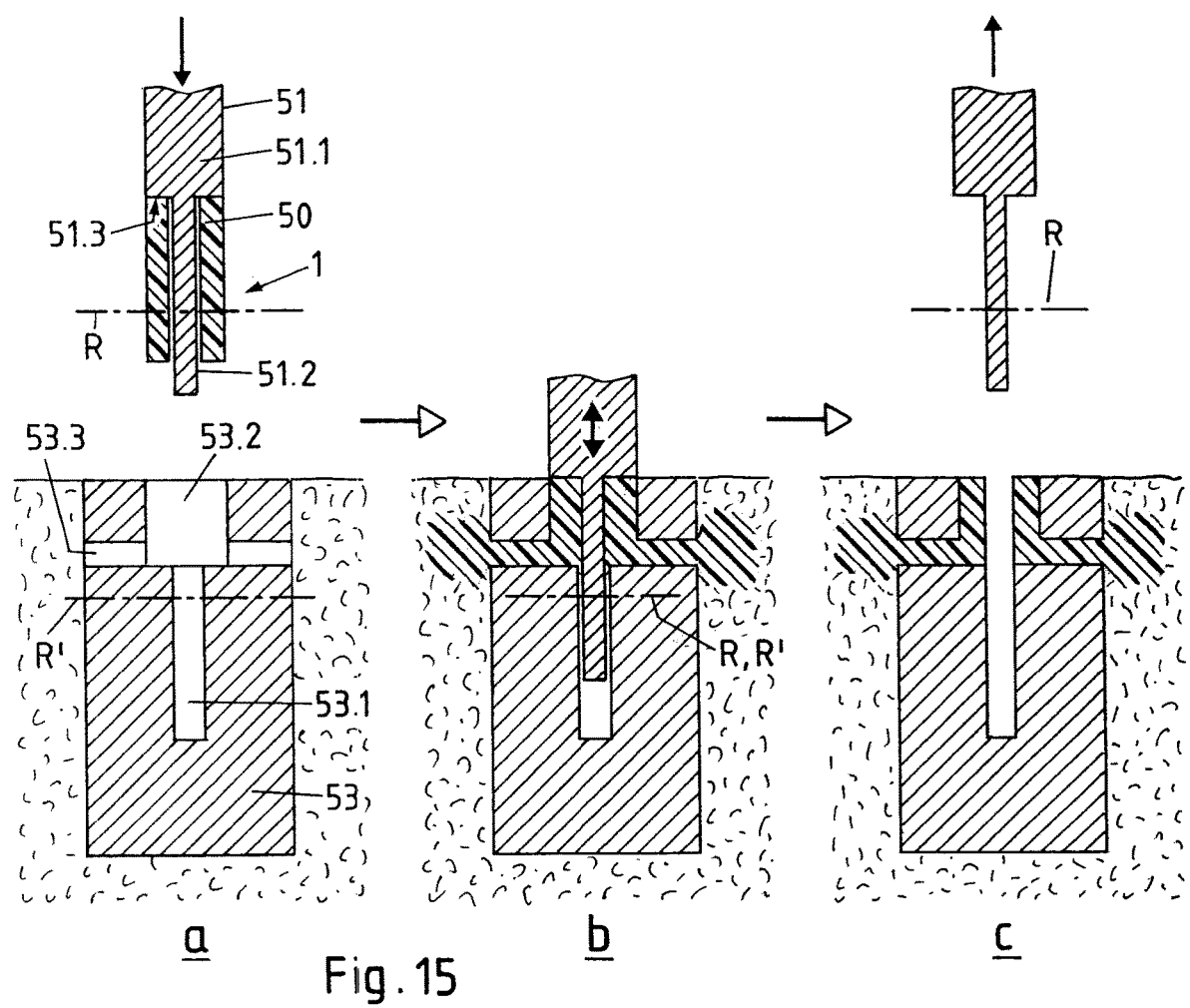
FIG. 15 illustrates device and method of the second aspect of the invention, wherein a sheath is anchored in a tissue opening with the aid of the liquefiable material.

FIG. 15 shows in three consecutive phases (a) to (c) an exemplary method for establishing an anchorage in tissue according to the second aspect of the invention, i.e. with the aid of a tube-shaped liquefiable part 50, again in connection with a vibrating element 51 and a perforated sheath 53.

The liquefiable part 50, which comprises the liquefiable material and preferably consist of it, has an inner and an outer cross section which may be circular or non-circular independent from each other. The vibrating element 51 preferably comprises a proximal portion 51.1 of a larger cross section, a distal portion 51.2 of smaller cross section and a shoulder 51.3 therebetween, wherein the cross section of the distal portion 51.2 is adapted to the inner cross section of the liquefiable part 50 and the cross section of the proximal portion 51.1 e.g. substantially the same as the outer cross section of the liquefiable part 50 and wherein the axial length of the distal portion 51.2 is e.g. at least as great as the axial length of the liquefiable part 50.

An inner space of the perforated sheath 53 comprises a step separating an inner region 53.1 from an outer region 53.2 and a step therebetween, wherein the cross section of the inner region 53.1 is substantially the same as the inner cross section of the liquefiable part 50 and the cross section of the outer region 53.2 is substantially the same as the outer cross section of the liquefiable part 50 (preferably clearance fit in both instances). The sheath perforations 53.3 are located in the outer region 53.2 of the inner sheath space, preferably adjacent to the step between the inner and outer region of the sheath inner space and they extend at any desirable angle relative to a sheath axis.

The liquefiable part 50 and the vibrating element 51 are preferably pre-assembled to form a tool 1, wherein e.g. the liquefiable part 50 is equipped with an inner thread and the distal portion 51.2 of the vibrating element 51 is equipped with a corresponding outer thread and wherein the liquefiable part 50 is screwed onto the vibrating element such that its proximal face is biased against the shoulder 51.3 of the vibrating element 51. The tool 1 comprising the vibrating element 51 and the liquefiable part 50 is coupled to a vibration source by rigidly connecting the proximal end of the vibrating element 51 to the vibration source (e.g. screw connection, chuck).

For anchoring the sheath 53 in tissue, a tissue opening is provided and the sheath is positioned therein such that outer mouths of the sheath perforations 53.3 are located close to the tissue wall of the opening. Phase (a) of FIG. 15 shows the sheath 53 positioned in the tissue opening and the pre-assembled tool 1.

Then the tool 1 is introduced into the sheath 53 such that a distal face of the liquefiable part 50 is in contact with the step of the inner sheath space. The vibration source is switched on and the tool 1 is pressed against the step to effect liquefaction of the liquefiable material at the interface between the distal face of the liquefiable part 50 and the step of the inner sheath space. The liquefied material flows from this interface through the sheath perforations 53.3 and penetrates the tissue adjacent the outer mouths of the perforations 53.3, wherein the tool is moved further into the inner sheath space for compensating the shortening of the liquefiable part 50 due to the liquefaction and flowing out.

The anchorage process is finished (phase (b)) when enough of the liquefiable material has been liquefied or when the proximal portion 51.1 being larger than the outer region of the inner sheath space reaches the proximal sheath face for the shoulder 51.3 to sit thereon. The vibration is then stopped.

The screwed connection between the liquefiable part 50 and the distal portion 51.2 of the vibrating element 51 is then loosened by e.g. turning the vibrating element by ca. 90 to 180° and, on further vibrating the vibrating element 51, the latter is pulled in an axial direction from the liquefiable part 50 to be removed from the now safely anchored sheath (phase (c)), whereby the thread at least of the liquefiable part 50 is destroyed.

If, as described above, the liquefiable part 50 is rigidly fixed to and even biased against the shoulder 51.3 of the vibrating element 51 the two act as one resonator, which guarantees liquefaction at the distal face of the liquefiable part 50 only, but requires tuning of the system including the liquefiable part 50. For such fixing co-operating threads as mentioned above may be provided on the liquefiable part 50 and the distal portion of the vibrating element 51, wherein the threads may extend along the whole length of the liquefiable part 50 and distal portion 51.2 of the vibrating element 51 or only along a part thereof. Instead of the named threads, it is possible also to fix the liquefiable part 50 to the distal portion of the vibrating element 50 by means of a press-fit and preferably a roughened surface on the side of the vibrating element, by a snap connection comprising e.g. cooperating grooves and ridges, by a bayonet coupling, by a self-locking cone coupling, or by similar connection means.

However, experiments show that even if the shoulder 51.3 is omitted or the threaded connection between the proximal portion 51.2 of the vibrating element 51 and the liquefiable part 50 is replaced by a push-fit connection (liquefiable part can be pushed onto the proximal part with an only small pushing force and does not come off by itself) a satisfactory anchorage can be achieved and without an undue amount of undesired melting at the proximal end of the liquefiable part 50, which may be further reduced by increasing the force used for holding the liquefiable part against the sheath and/or by providing the sheath inner surface at the interface with the liquefiable part with energy directors and/or providing the liquefiable part with a tapering distal end for reducing its contact area with the sheath inner surface. With such measures it will even be possible to carry out the anchoring process according to FIG. 15 with a liquefiable part 50 which sits only loosely on the distal portion 51.2 of the vibrating element 51.

In any of the above listed cases less of the named undesirable liquefaction occurs in comparison with the per se known anchoring method in which a solid pin of the liquefiable material is pressed into the sheath. This finding is thought to be due to the exact guidance of the vibrating part 51 relative to the liquefiable part 50 by the distal portion 51.2 of the vibrating part which according to FIG. 15 extends through the liquefiable part right into the inner portion 53.1 of the inner sheath space. Such guidance acting on the whole of the liquefiable part gives optimum results. However, experiments show that guidance at the proximal end of the liquefiable part is more important than guidance at the distal end and therefore, the axial length of the distal portion 51.2 of the vibrating part 51 may be reduced. For still a satisfactory effect, a minimum length of this distal portion is such that it reaches into the liquefiable part to a region which is located in the sheath when the liquefiable part is positioned in the sheath ready for the anchoring process. A distal portion 51.2 of the vibrating element 51 having a reduced axial length will allow the inner portion of the sheath's inner space to be less deep or to be omitted entirely. The axial length of a reduced distal part 51.2 and the correspondingly reduced depth of the inner portion of the sheath's inner space respectively is shown in FIG. 15 with dash-dotted lines denominated with R and R' respectively.

Device and method according to FIG. 15 are e.g. applicable for mounting a cage in an intervertebral space. In this application the cage represents the sheath and preferably comprises more than one inner space, e.g. two laterally spaced inner spaces. From each inner space perforations or fenestrations lead to an upper and a lower surface of the cage, wherein these upper and lower surfaces are to be in contact with the vertebral bodies between which the cage is to be fixed. During the anchoring process the liquefied material of the liquefied part flows through the perforations into the bone tissue of the vertebral bodies, which for better penetration of the liquefied material are preferably locally decorticated.

FIG. 16 shows a similar embodiment of the further aspect of the invention as FIG. 15, wherein same elements are designated with the same reference numerals. Other than according to FIG. 15, the inner space of the sheath 53 comprises two steps and the liquefiable part 50 comprises two portions dimensioned for being pressed against the two steps either after each other, as illustrated, or simultaneously. The sheath 53 comprises perforations 53.3 in the vicinity of both steps. The anchoring process is carried out as above described in connection with FIG. 15.

FIG. 17 shows again a similar embodiment of the second aspect of the invention as FIG. 15, wherein same elements are designated with same reference numerals. Other than according to FIG. 15, the guiding function of the distal portion 51.2 of the vibrating element 51 is taken over by a separate, guide element 55 (e.g. floating pin or guide wire) which extends through the liquefiable part 50 into the inner region 53.1 of the inner sheath space or at least to the bottom of the outer region thereof and on the proximal side reaches into a corresponding recess 51.5 in the vibrating part 51. The guide element 55 is e.g. dimensioned such that it fits loosely or with a push fit into the named elements. For the anchoring step, the liquefiable part 50 is positioned on the step of the inner sheath space, the guide element 55 is positioned through the liquefiable part 50 into the inner region 53.1 of the inner sheath space and the vibrating element 51 is positioned such that it is in contact with the proximal face of the liquefiable part 50 and that a proximal portion of the guide element 55 extends into its recess 51.5.

It is possible also to fix the guide element 55 in the liquefiable part 50 e.g. by providing co-operating threads on both. Such the liquefiable part 50 and the guide element 55 can be handled as one. After the anchoring process, the proximal portion of the guide element 55 is trimmed off and the distal portion is left together with the liquefiable part 50 in the anchored sheath 51.

The guide element 55 may be constituted by a K-wire which is used also for creating the tissue opening in which the sheath is positioned. Such a K wire may extend through a correspondingly open distal end of the sheath and through the entire vibrating element as shown in FIG. 17 with dash-dotted lines.

FIG. 18 shows again a similar embodiment of the further aspect of the invention as FIG. 15, wherein same elements are designated with same reference numerals. Other than according to FIG. 15, there is no sheath, but instead the liquefiable part 50 is anchored in the tissue opening directly and constitutes the only anchored part. The left hand side of FIG. 18 shows the opening provided in the tissue which regarding shape and dimensions corresponds to the inner sheath space according to FIGS. 15 to 17, and the pre-assembled tool 1 comprising the vibrating element 51 and the liquefiable part 50 which may be fixed on the distal portion 51.2 of the vibrating element 51 or sit thereon with a push fit or loosely as discussed in connection with FIG. 15. The right hand side of FIG. 18 shows the arrangement after completion of the anchorage process and before removal of the vibrating element 51 from the anchored liquefiable part 50.

Combinations of features of the anchoring method and device described above in connection with a plurality of embodiments of the invention can be combined differently by one skilled in the art without causing difficulties. Such different combinations do not depart from the basic idea of the invention.

What is claimed is:

1. A method for supplying a material having thermoplastic properties and being liquefiable by mechanical vibration to an operating site with the aid of mechanical vibration and a material which is liquefiable by the mechanical vibration, the method comprising the steps of:

providing a device comprising a vibrating element and a tube-shaped liquefiable part, wherein the vibrating element comprises a distal portion being a guide element, and a proximal portion, a proximal end of the vibrating element being suitable for being coupled to a vibration source, and the vibrating element being capable of transmitting vibration generated by the vibration source to a distal end of the vibrating element, wherein the tube-shaped liquefiable part comprises the liquefiable material and has an inner and an outer cross section, wherein the guide element of the vibrating element is dimensioned for extending through the tube-shaped liquefiable part, coupling the device to the vibration source, providing a tissue opening of which at least an outer portion has a cross section which is adapted to the outer cross section of the liquefiable part, positioning a distal portion of the device in the tissue opening such that a distal face of the liquefiable part sits on a bottom or on a step of the tissue opening and that the guide element of the vibrating element reaches into the tissue opening wherein the proximal portion reaches into a corresponding recess in the vibrating element, switching on the vibration source and pressing the device against the step of the tissue opening for a time sufficient for liquefying at least a part of the liquefiable material and making it penetrate into the tissue, switching off the vibration source and removing the vibrating element from the liquefiable part and the tissue;

wherein the guide element is fixed in the liquefiable part.

2. The method according to claim 1, wherein the guide element is a separate guide element.

3. The method according to claim 2, wherein the separate guide element is dimensioned to fit loosely or with a push fit into the recess of the vibrating element.

4. The method according to claim 2, wherein the separate guide element is constituted by a K-wire.

5. The method according to claim 1, wherein the guide element is fixed in the liquefiable part with co-operating threads.

6. The method according to claim 1, wherein the guide element is constituted by a K-wire.

* * * * *